US005955058A

United States Patent [19]
Jager et al.
[11] Patent Number: 5,955,058
[45] Date of Patent: Sep. 21, 1999
[54] STABILIZED MEDICINAL AEROSOL SOLUTION FORMULATIONS CONTAINING IPRATROPIUM BROMIDE

[75] Inventors: Paul Donald Jager, Waterbury; Mark James Kontny, New Milford, both of Conn.; Jurgen Hubert Nagel, Ingelheim/Rhein, Germany

[73] Assignee: Boehringer Ingelheim Pharmaceuticals, Inc., Ridgefield, Conn.

[21] Appl. No.: 08/843,180

[22] Filed: Apr. 14, 1997

Related U.S. Application Data

[63] Continuation of application No. 08/475,060, Jun. 7, 1995, Pat. No. 5,676,930, which is a continuation of application No. 08/153,549, Nov. 22, 1993, abandoned, which is a continuation-in-part of application No. 07/987,852, Dec. 9, 1992, abandoned.

[51] Int. Cl.$^6$ .................... A61K 9/12

[52] U.S. Cl. .................... 424/45; 424/46

[58] Field of Search .................... 424/45, 46

[56] References Cited

U.S. PATENT DOCUMENTS

| | | | |
|---|---|---|---|
| 5,118,494 | 6/1992 | Schultz et al. | 424/45 |
| 5,190,029 | 3/1993 | Byron et al. | 128/200.14 |
| 5,225,183 | 7/1993 | Purewal et al. | 424/45 |
| 5,439,670 | 8/1995 | Purewal et al. | 424/45 |
| 5,605,674 | 2/1997 | Purewal et al. | 424/45 |

FOREIGN PATENT DOCUMENTS 0372 777 6/1990 European Pat. Off. .

*Primary Examiner*—Raj Bawa
*Attorney, Agent, or Firm*—Morgan & Finnegan, LLP

[57] ABSTRACT

Stabilized medicinal aerosol solution formulations comprising medicaments that degrade or decompose by interaction with solvents or water, an HFC propellant, a cosolvent and an acid are described. Further, specific medicinal aerosol solution formulations comprising ipratropium bromide or fenoterol, ethyl alcohol, 1,1,1,2-tetrafluoroethane or 1,1,1,2,3,3,3-heptafluoropropane, and either an inorganic acid or an organic acid are described. The acids are present in amounts sufficient to reduce the degradation of the medicaments to acceptable levels.

28 Claims, 1 Drawing Sheet

STABILIZED MEDICINAL AEROSOL SOLUTION FORMULATIONS CONTAINING IPRATROPIUM BROMIDE

This application is a continuation of U.S. Ser. No. 08/475,060, Jun. 7, 1995, now U.S. Pat. No. 5,676,930 which is a continuation of U.S. Ser. No. 08/153,549, Nov. 22, 1993, abandoned, which is a continuation-in-part of U.S. Ser. No. 07/987,852, Dec. 9, 1992, abandoned.

This invention relates to stable pharmaceutical solution formulations suitable for aerosol administration. More particularly, this invention relates to stable pharmaceutical solution formulations suitable for aerosol administration wherein either an inorganic acid or an organic acid is added to the aerosol solution formulation which contains a medicament in solution with an environmentally safe hydrofluorocarbon (HFC) as a propellant, together with an organic compound as a cosolvent. The acid provides stability against degradation or decomposition of the medicament resulting largely from interaction of the medicament with the cosolvent and/or water present in the solution formulation.

BACKGROUND OF THE INVENTION

The administration of aerosol formulations of medicaments by means of pressurized, metered-dose inhalers (MDIs) is used widely in therapy, such as in the treatment of obstructive airway diseases and asthma. Compared with oral administration, inhalation provides more rapid onset of action while minimizing systemic side effects. Aerosol formulations can be administered by inhalation through the mouth or topically by application to the nasal mucosa.

Formulations for aerosol administration via MDIs can be solutions or suspensions. Solution formulations offer the advantage of being homogeneous in nature with the medicament and excipient completely dissolved in the propellant vehicle. Solution formulations also obviate physical stability problems associated with suspension formulations and thus assure more consistent uniform dosage administration while also eliminating the need for surfactants.

The administration of aerosol solution formulations via MDIs is dependent upon the propulsive force of the propellant system used in its manufacture. Traditionally, the propellant comprised a mixture of chlorofluorocarbons (CFCs) to provide the desired solubility, vapor pressure, and stability of the formulation. However, since it has been established in recent years that CFCs are environmentally harmful because they contribute to the depletion of the Earth's ozone layer, it is desirable to substitute environmentally safe hydrofluorocarbon (HFC) propellants or other non-chlorinated propellants for environmentally harmful CFC propellants in aerosol inhalation formulations. For example, U.S. Pat. No. 4,174,295 discloses the use of propellant systems consisting of combinations of HFCs, which may also contain a saturated hydrocarbon component, suitable for application in the fields of home products such as hair lacquers, anti-perspiration products, perfumes, deodorants, paints, insecticides and the like.

It is known in the art that certain HFCs have properties suitable for use as propellants for the aerosol administration of medicaments. For example, published European patent Application No. 0 372 777 (EPO89312270.5) describes the use of 1,1,1,2-tetrafluoroethane (HFC-134(a)) in combination with at least one "adjuvant" (a compound having a higher polarity than the HFC-134(a)) and a surface active agent to prepare suspension and solution formulations of medicaments suitable for administration by the aerosol route. Also, PCT Published Application No. WO91/11496 (PCT/EP91/00178) discloses the use of 1,1,1,2,3,3,3-heptafluoropropane (HFC-227), optionally mixed with other propellant components, for use in preparing suspension aerosol formulations of medicaments.

It has now been found that the use of propellant systems containing an HFC and a cosolvent in aerosol solution formulations presents a chemical stability problem that has not been previously recognized or resolved in the prior art. This is because in such HFC propellant/cosolvent systems, the medicament may interact with the cosolvent and/or water present in the system to produce decomposition or degradation products. It has now further been found that the addition of an acid, either an inorganic acid or an organic acid, to the HFC propellant/cosolvent system provides the requisite chemical stability to the medicament.

DESCRIPTION OF THE INVENTION

Figure 1:
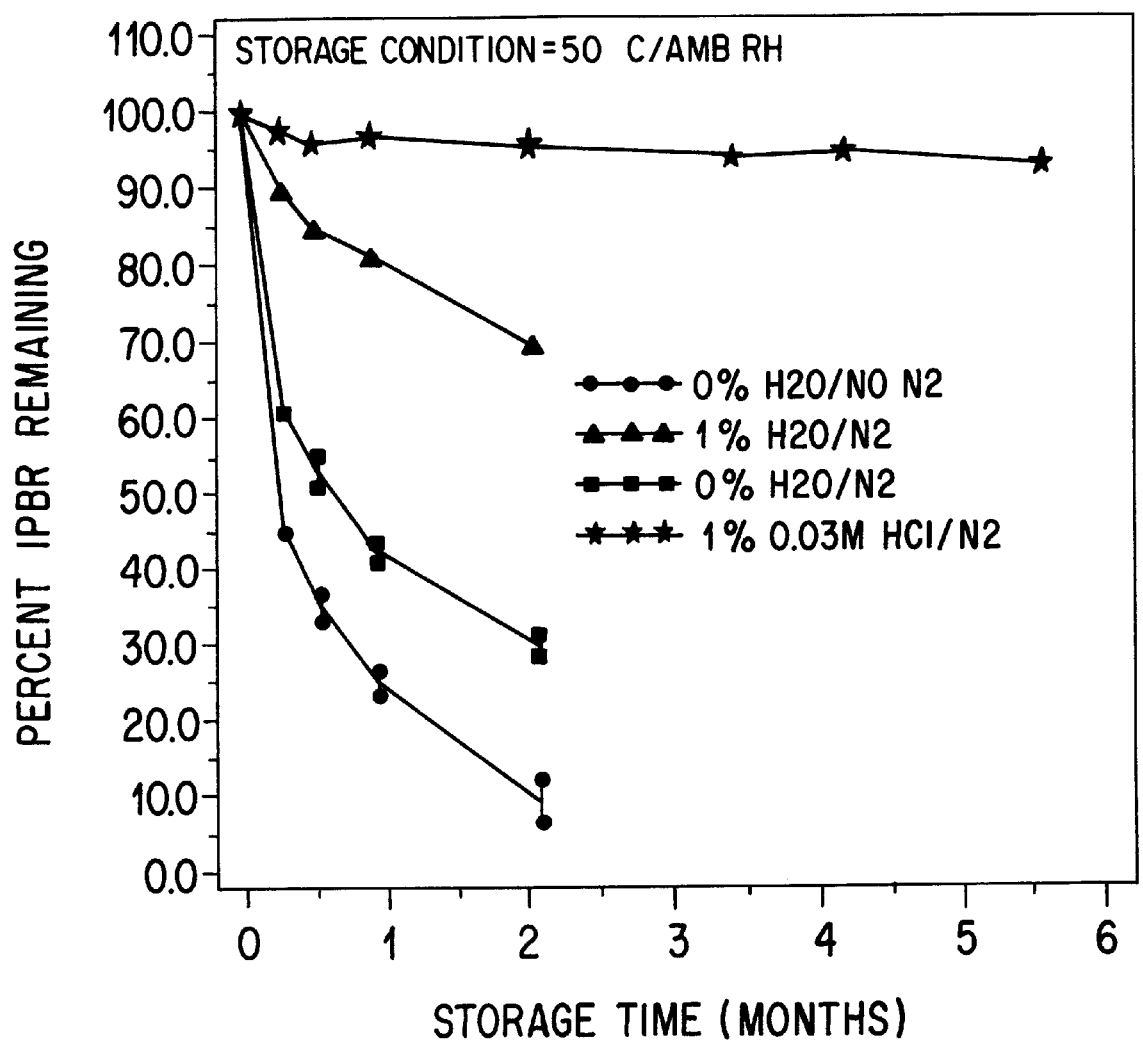
FIG. 1 depicts the stability profiles of ipratropium bromide aerosol solutions.

The term "aerosol suspension formulation" means a pharmaceutical formulation of a medicament suitable for aerosol administration wherein the medicament is suspended, in the form of finely, divided particles, in an excipient.

The term "aerosol solution formulation" means a pharmaceutical formulation of a medicament suitable for aerosol administration wherein the medicament and excipients are completely dissolved.

The term "stabilized aerosol solution formulation" means an aerosol solution formulation which exhibits substantial chemical stability over time.

Ipratropium bromide is an anticholinergic bronchodilator marketed under the trademark "ATROVENT." This medicament is administered as an aerosol suspension formulation which contains a mixture of CFCs (dichlorodifluoromethane, dichlorctetrafluoroethane, and trichloromonofluoromethane) as the propellant, and soya lecithin.

Studies have demonstrated that stable aerosol solution formulations of ipratropium bromide can be obtained by dissolving ipratropium bromide in a homogeneous system comprising HFC-134(a), ethanol, and either an inorganic acid or an organic acid. The particular type and amount of acid added to the system will define the level of acidity which is critical in obtaining a stable solution formulation.

Thus, the present invention provides stabilized aerosol solution formulations comprising a medicament, an HFC propellant, a cosolvent, and an inorganic acid or an organic acid. A small amount of water (up to about 5% by weight) may also be present in the propellant/cosolvent system.

Suitable HFC propellants are those which, when mixed with the cosolvent(s), form a homogeneous propellant system in which a therapeutically effective amount of the medicament can be dissolved. The HFC propellant must be toxicologically safe and must have a vapor pressure which is suitable to enable the medicament to be administered via a pressurized MDI. Additionally, the HFC propellant must be compatible with the components of the MDI device (such as containers, valves, and sealing gaskets, etc.) which is employed to administer the medicament. Preferred HFC propellants are 1,1,1,2-tetrafluoroethane (HFC-134(a)) and 1,1,1,2,3,3,3-heptafluoropropane (HFC-227). HFC-134(a) is particularly preferred. Other examples of HFC propellants are HFC-32 (difluoromethane), HFC-143(a) (1,1,1-trifluoroethane), HFC-134 (1,1,2,2-tetrafluoroethane), and HFC-152a (1,1-difluoroethane).

It will be apparent to those skilled in the art that non-halogenated hydrocarbon propellants may be used in place of the HFC propellants in the present invention. Examples of non-halogenated hydrocarbons are saturated hydrocarbons, including propane, n-butane, and isobutane, and ethers, including diethyl ether.

It will also be apparent to those skilled in the art that, although the use of a single HFC propellant is preferred, a mixture of two or more HFC propellants, or a mixture of at least one HFC propellant and one or more non-CFC propellants, may be employed in the aerosol solution formulation of the present invention.

A substantially non-aqueous HFC propellant/cosolvent system is preferred. Water may be present in small amounts as an impurity in the HFC propellant/cosolvent system, may be introduced during the manufacturing process or may permeate into the system through the valve or valve/container seals or gaskets. If desired, small amounts of water may be added (up to about 5% by weight) to the HFC/propellant system, for example, to aid in manufacturing.

If desired, pharmaceutically acceptable excipients can be included in the aerosol solution formulations of the present invention. For example, a soluble surface active agent can be added in order to improve the performance of valve systems employed in the MDI devices used for the aerosol administration of the formulations. Examples of preferred surface active agents are oleic acid, sorbitan trioleate, lecithin, and isopropylmyristate. Other suitable lubricants are well known in the art (see, for example, Published European Patent Application No. 0372777 (EPO 893122705)). Other excipients are: (a) antioxidants, for example ascorbic acid and tocopherol; (b) taste masking agents, for example, menthol, sweeteners, and artificial or natural flavors; and (c) pressure modifying agents, for example, n-pentane, iso-pentane, neo-pentane, and n-hexane.

The medicaments used in the present invention may be any substance which is suitable for aerosol administration from an MDI or similar device. The medicament must be soluble in the HFC propellant/cosolvent system and, characteristically exhibit significant degradation or decomposition in the HFC propellant/cosolvent system. The degradation or decomposition of the medicament must be acid sensitive in that the rate of degradation or decomposition can be effectively reduced by the addition of acid.

The decomposition and the degradation of the medicament may occur by various chemical mechanisms, the most significant being interaction of the medicament with the cosolvent or with the water present in the system to form hydrolysis, esterification, and/or ether products.

The amount of medicament employed in the aerosol solution formulations of the present invention is that which is effective in producing the intended therapeutic effect, i.e., an amount such that one or more metered volumes of the formulation will deliver an effective amount of the medicament. It will be apparent to those skilled in the art that the potency of the particular medicament employed in the aerosol solution formulation will determine the amount of medicament in the formulation. In general, the medicament is present in an amount from about 0.001 to 10 percent by weight of the total weight of the formulation. An amount of from about 0.01 to 1.0 percent by weight of the total weight of the formulation is preferred.

Bronchodilators (in particular anticholinergics and sympathomimetics) are the preferred class of medicaments for use in the aerosol solution formulations of the present invention. Those skilled in the art will recognize that other classes of medicaments can in general be used. Examples of such classes are: antihistamines, antiallergics, antiinflammatories, PAF-antagonists, antitussives, antibiotics, mast cell stabilizers, mucolytics, antineoplastics, antiinfectives, vaccines, anesthetics, diagnostic agents, analgesics, antianginals, leukotriene antagonists, and 5-lipoxygenase antagonists. The medicaments can also be various types of organic molecules, including, but not limited to, hormones, enzymes, proteins, peptides, steroids, alkaloids, or combinations thereof.

The most preferred example of the medicaments for use in the aerosol solution formulations of the present invention is ipratropium bromide. Other preferred examples are oxitropium bromide (BA253), albuterol, metapraterenol sulfate, tiotropium bromide (BA-679), 8-azoniabicyclo[3.2.1]oct-6-ene, 3-[(hydroxydi-2-thienylacetyl)oxy]-8,8-dimethyl-, chloride, endo- (BEA 2108 CL), and fenoterol hydrobromide.

Other examples of medicaments are:
Symnathomimetic Bronchodilators:
   (a) alpha-adrenergic agonists: ephedrine, epinephrine, norfenefrine, phenylephrine, and phenylpropanolamine.
   (b) beta-adrenergic agonists: bambuterol, bitoterol, carbuterol, clenbuterol, ephedrine, formoterol, hexoprenaline, isoproterenol, mabuterol, pirbuterol, reproterol, rimiterol, terbutaline, and tulobuterol.
Anticholinergic Bronchodilators: telenzepine, troventol, and flubron.
Alkaloids: atropine, scopolamine, and bromocriptine.

The medicaments used in the present invention may be in the form of either the free base or a pharmaceutically acceptable, non-toxic, salt thereof. Suitable salts are well known in the pharmaceutical and medicinal arts. The selection of a particular salt will depend upon the chemical nature of the base and the chemical stability and solubility of the salt in the formulation. Examples of salts that may be employed are: acetate, benezenesulphonate, benzoate, bicarbonate, bitartrate, bromide, calcium edentate, camsylate, esylate, fumarate, fluceptate, gluconate, glutamate, glycolarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methysulfate, mucate, napsylate, nitrate, pamoate (embonate), pantothenate, phosphate/diphosphate, polygalacturonate, salicylate, stearate, subacetate, succinate, sulphate, tannate, tartrate, and triethiodide. Cationic salts may also be used. Examples of cationic salts include the alkali metals, e.g. sodium and potassium, and ammonium salts and salts of amines known to be pharmaceutically acceptable, e.g., glycine, ethylene diamine, choline, diethanolamine, triethanolamine, octadecylamine, diethylamine, triethylamine, 1-amino-2-propanol-amino-2-(hydroxymethyl) propane-1,3-diol and 1-3(3,4-dihydroxyphenyl)-2-isopropylaminoethanol.

The chemical nature of the medicament defines the nature of the cosolvent, which may be any one of a number of organic solvents that are toxicologically safe and amenable to MDI solution formulations. By "cosolvent" is meant any solvent which is miscible in the formulation in the amount desired and which, when added provides a formulation in which the medicament can be dissolved in therapeutically effective amounts. Examples of cosolvents that contain hydroxyl functions (or other functions) capable of interacting with the medicament(s) in the formulation are: alcohols, for example, ethyl alcohol and isopropyl alcohol; glycols for example, propylene glycol, polyethylene glycols, polypropylene glycols, glycol ethers, and block copolymers of oxyethylene and oxypropylene; and other substances, for example, glycerol, polyoxyethylene alcohols, and polyoxtethylene fatty acid esters.

Examples of cosolvents that may be inert to interaction with the medicament(s) are hydrocarbons, for example, n-propane, n-butane, isobutane, n-pentane, iso-pentane, neo-pentane, and n-hexane; and ethers, for example, diethyl ether.

A preferred cosolvent according to this invention is ethyl alcohol (ethanol).

The function of the cosolvent is to increase the solubility of the medicament and the excipients in the formulation. Thus, the amount of cosolvent present in the formulation defines the maximum amount of medicament and excipients that can be dissolved at a particular temperature.

The selection of the acid in the aerosol solution formulations of this invention depends on the medicament used and the acid concentration needed to effect an acceptable rate of degradation of the medicament. Ideally the preferred acid will have the same anion as that contained in the medicament, if any. However, in some instances, this may present solubility limitations. The acid may be any inorganic or mineral acid, for example, hydrochloric acid, sulfuric acid, nitric acid, or phosphoric acid, or the like. The acid may also be selected from the group of acids known to those skilled in the art as organic acids, which are in most cases considered to be weak acids relative to the inorganic acids. Representative of this group and preferred in this invention are ascorbic acid and citric acid, although other organic acids may also be suitable. However, according to this invention, citric acid is the most preferred acid because of MDI component compatibility.

According to this invention an aerosol solution formulation comprising a particular medicament may be formulated using acids selected from either of the above groups.

The methods used to introduce the acid into the formulation may include: (1) the direct addition of the inorganic or organic acid; (2) the addition of the medicament as an acidic salt thereby generating the correct acidity level in situ, and (3) combinations of (1) and (2). Appropriate salts for introducing the medicament into the formulation will be apparent to those skilled in the art.

Laboratory experiments have demonstrated that aerosol solution formulations of ipratropium bromide in HFC-134 (a) and about 35% ethanol exhibit significant decomposition of the ipratropium bromide when stored at 50° C. The decomposition can be attributed to oxidation, chemical dehydration, hydrolysis and esterification. However, tropic acid ethyl ester is the chief degradation product. This ester can be formed by the direct reaction of ethanol with ipratropium bromide or by hydrolysis of ipratropium bromide followed by esterification of tropic acid with ethanol. Addition of 1% water reduced the decomposition due to dehydration. Carrying out the reaction under nitrogen atmosphere reduced the oxidation products.

In aqueous solution the rate of hydrolysis and esterification is typically pH dependent. In aqueous solution, the degradation of ipratropium bromide exhibits a pH-rate minimum at pH 3.5. This corresponds to a hydrogen ion concentration of $3.2 \times 10^{-4}$ molar (M) at 25° C. Although the concept of pH is poorly defined in non-aqueous systems, formulation evaluation studies were conducted using this concentration of hydrochloric acid in the HFC-134(a)/ethanol system containing ipratropium bromide. Samples stored at 50° C. for five and one-half months exhibited less than 5.5% loss of ipratropium bromide. A summary of these results is illustrated in FIG. 1.

A range of chemical compositions is given in Table 1 for aerosol solution formulations containing ipratropium bromide, HFC-134(a), and an inorganic acid, such as hydrochloric, nitric phosphoric, or sulfuric acid. The amount of alcohol present in the formulation defines the maximum amount of ipratropium bromide that can be dissolved at a particular temperature. The range of ipratropium bromide concentrations given in Table 1 is based on the maximum amount that can be safely dissolved without precipitation at room temperature for a given alcohol concentration. Acid content is given in units of normality which defines a pH range equivalent to 2.0–4.7 in an aqueous system.

TABLE 1

Ipratropium Bromide Aerosol Solution Formulations:
Range Of Chemical Compositions For An Inorganic Acid Formulation

| Component | Contents per MDI Container |
| --- | --- |
| Ipratropium Bromide as the Monohydrate | 0.001–2.5% wght./wght. |
| Dehydrated (Absolute) Ethanol, USP | 1.0–50.0% wght./wght. |
| 1, 1, 1, 2-Tetrafluoroethane, (HFC-134(a)) (Dupont Pharmaceutical Toxicity Grade) | 50.0–99.0% wght./wght. |
| Inorganic Acid, USP/NF (Hydrochloric Acid) | 0.01–0.00002 Normal |
| Water (Purified), USP | 0.0–5.0% wght./wght. |

A range of chemical compositions is given in Table 2 for aerosol solution formulations containing ipratropium bromide, HFC-134(a), and the organic acid, ascorbic acid. The range of ascorbic acid concentration presented in Table 2 was based on its acid dissociation constant(s), pKa(s), and the optimal pH range for a stable ipratropium bromide formulation (2.0–4.7) in an aqueous system. For ascorbic acid, 0.0045–275 mg/ml would be required to correspond to an aqueous pH range of 2.0–4.7. However, solubility limitations in the formulation must also be taken into consideration given the fact that ascorbic acid is only soluble to about 20 mg/ml in absolute ethanol and is expected to have a lesser solubility in an absolute ethanol/HFC-134(a) system. The information contained in Table 2 is presented for ascorbic acid and gives a range of ethanol content that is based on the expected room temperature solubility of ipratropium bromide (as the monohydrate). Optimally, about 0.30 mg/ml of ascorbic acid is expected to be required in such a formulation corresponding to a pH-degradation rate minimum of pH 3.5 for ipratropium bromide in an aqueous system.

The range of concentration presented in Table 2 for ascorbic acid will differ for another organic acid depending on its acid dissociation constant(s). For example about 0.0039–27.7 mg/ml of citric acid would be required in the formulation corresponding to an optimal aqueous pH range of 2.0–4.7 for ipratropium bromide.

The range of acid concentration required to effect an acceptable rate of decomposition for medicaments in primarily non-aqueous solution aerosol formulations will depend primarily on the chemical composition of the formulation (such as choice of cosolvent(s) and the chemical nature of the medicaments(s) present). This range is expected to be about 0.10–0.0000001 normal for the inorganic acids corresponding to an aqueous pH range of about 1.0–7.0 and must be calculated for the organic acids depending on their pKa values.

TABLE 2

Ipratropium Bromide Aerosol Solution MDI Formulations:
Range Of Chemical Compositions For An Organic Acid Formulation

| Component | Contents per Container |
|---|---|
| Ipratropium Bromide as the Monohydrate | 0.001–2.5% wght./wght. |
| Dehydrated (Absolute) Ethanol, USP | 1.0–50.0% wght./wght. |
| 1, 1, 1, 2-Tetrafluoroethane, (HFC-134(a)) (Dupont Pharmaceutical Toxicity Grade) | 50.0–99.0% wght./wght. |
| Ascorbic Acid, USP | 0.00015–5.0 mg/ml |
| Water (Purified), USP | 0.0–5.0% wght./wght. |

Preferred examples of chemical compositions for aerosol solution formulations containing ipratropium bromide, HFC-134(a) and citric acid are shown in Table 3. The standard amount of ipratropium bromide in an MDI which is considered to supply an effective dosage is indicated as "regular strength." However, dosages of half strength and double strength are also preferred. The range of citric acid concentration presented in Table 3 was based on its acid dissociation constant(s), pKa(s), and optimal pH range for a stable ipratropium bromide formulation (2.0–4.7) in an aqueous system.

TABLE 3

Ipratropium Bromide Aerosol Solution Formulations Containing Citric Acid

| | Contents per MDI Container | | |
|---|---|---|---|
| Component | Half Strength | Regular Strength | Double Strength |
| Ipratropium Bromide as the Monohydrate | 0.0187% wght./wght | 0.0374% wght./wght. | 0.0748% wght./wght. |
| Dehydrated (Absolute) Ethanol, USP | 15.0000% wght./wght | 15.0000% wght./wght | 15.0000% wght./wght |
| 1, 1, 1, 2-Tetrafluoroethane, (HFC-134(a)) (Dupont Pharmaceutical Toxicity Grade) | 84.4773% wght./wght. | 84.4586% wght./wght. | 84.4212% wght./wght. |
| Citric Acid, USP | 0.0040% wght./wght. | 0.0040% wght./wght. | 0.0040% wght./wght. |
| Water (Purified), USP | 0.5000% wght./wght. | 0.5000% wght./wght. | 0.500% wght./wght. |
| Total | 100.0000% | 100.0000% | 100.0000% |

As another preferred example, Table 4 gives a chemical composition for an aerosol formulation containing fenoterol hydrobromide, HFC-134(a) and citric acid.

TABLE 4

Fenoterol Hydrobromide Aerosol Solution Formulation

| Component | Contents per MDI Container |
|---|---|
| Fenoterol Hydrobromide | 0.192% wght./wght. |
| Dehydrated (Absolute) Ethanol, USP | 30.000% wght./wght. |
| 1, 1, 1, 2-Tetrafluoroethane, (HFC-134(a)) (Dupont Pharmaceutical Toxicity Grade) | 67.806% wght./wght. |
| Citric Acid, USP | 0.002% wght./wght. |
| Water (Purified), USP | 2.000% wght./wght. |
| Total | 100.000% |

The amount of drug in an aerosol solution formulation that can be delivered through the valve of an MDI will depend on the activeingredient concentration (mg/ml) in the formulation and the metering volume (ul) of the valve. Commonly used valve sizes are 25, 50, 63 and 100 ul.

Metered dose inhalers containing aerosol solution formulations of medicaments can be manufactured using a number of conventional processing methods. One method, which is useful in the laboratory for the manufacture of small laboratory scale lots, is Dual Stage Pressure Fill. This method is shown in Tables 5 and 6 for two specific ipratropium bromide solution formulations using a 50-ul valve. Two methods for large scale manufacture are Single-Stage Cold Fill and Single-Stage Pressure Fill.

TABLE 5

Ipratropium Bromide Inhalation Aerosol, 0.021 mg Drug Delivered Through The Valve, 12 ml I. Composition

| Component | Contents per Container |
|---|---|
| Ipratropium Bromide Monohydrate | 0.00505 gm |
| Dehydrated (Absolute) Ethyl Alcohol, USP | 2.02500 gm |
| 1, 1, 1, 2-Tetrafluoroethane, (HFC-134(a) (Dupont Pharmaceutical Toxicity Grade) | 11.40209 gm |
| Nitric Acid, USP/NF | 0.00036 gm |
| Water (Purified), USP | 0.06750 gm |
| TOTAL: | 13.50000 |

II. Device Components
  Suitable Aerosol Container
  50 ul Aerosol Metering Valve
III. Brief Description of Processing Method
  An active ingredient concentrate is prepared by dissolving the ipratropium bromide, as the monohydrate, nitric acid, and water in ethyl alcohol. The concentrate is added to an appropriate filling apparatus. The active ingredient concentrate is dispensed into aerosol containers. The headspace of the containers is purged with nitrogen or HFC-134(a) vapor (purging ingredients should not contain more than 1 ppm oxygen) and is sealed with valves. The HFC-134(a) propellant is then pressure-filled into the sealed containers.

TABLE 6

Ipratropium Bromide Inhalation Aerosol, 0.021 mg Drug Delivered Through The Valve, 12 ml I. Composition

| Component | Stated Contents Per Container |
|---|---|
| Ipratropium Bromide Monohydrate | 0.00505 gm |
| Dehydrated (Absolute) Ethyl Alcohol, USP | 2.02500 gm |
| 1, 1, 1, 2-Tetrafluoroethane (HFC-134A), (Dupont Pharmaceutical Toxicity Grade) | 11.26745 gm |
| Ascorbic Acid, USP | 0.13500 gm |
| Water (Purified), USP | 0.06750 gm |
| TOTAL: | 13.50000 |

II. Device Components:
  Suitable Aerosol Container
  50 ul Aerosol Metering Valve
III. Brief Description of Processing Method
  An active ingredient concentrate is prepared by dissolving the ipratropium bromide, as the monohydrate, ascorbic acid and water in ethyl alcohol. The concentrate is added to an appropriate filling apparatus. The active ingredient concentrate is dispensed into aerosol containers, the headspace of the containers is purged with Nitrogen or HFC-134(a) vapor (purging ingredients should not contain more than 1 ppm oxygen) and is sealed with valves. The HFC-134(a) propellant is then pressure filled into the sealed containers.

What is claimed is:

1. An aerosol solution formulation comprising from 0.001% to about 10% wt/wt ipratropium bromide, a hydrofluorocarbon propellant, an organic cosolvent, and an inorganic acid.

2. An aerosol solution according to claim 1 wherein the propellant is 1,1,1,2-tetrafluoroethane.

3. An aerosol solution formulation according to claim 2 wherein the organic cosolvent is ethyl alcohol.

4. An aerosol solution formulation according to claim 3 wherein the ethyl alcohol is in the range of about 1.0 to 50.0% wght./wght. of the formulation.

5. An aerosol solution formulation according to claim 3 wherein the inorganic acid is selected from the group consisting of sulfuric acid, hydrochloric acid, nitric acid, and phosphoric acid.

6. An aerosol solution formulation according to claim 3 which contains water in an amount up to about 5.0% wght./wght.

7. An aerosol solution formulation according to claim 1 wherein the propellant is 1,1,1,2,3,3,3-heptafluoropropane.

8. An aerosol solution formulation according to claim 7 wherein the organic cosolvent is ethyl alcohol.

9. An aerosol solution formulation according to claim 8 wherein the ethyl alcohol is in the range of about 1.0 to 50.0% wght./wght. of the formulation.

10. An aerosol solution formulation according to claim 8 wherein the inorganic acid is selected from the group consisting of sulfuric acid, hydrochloric acid nitric acid, and phosphoric acid.

11. An aerosol solution formulation comprising 0.001% to about 10 wt % ipratropium bromide, a hydrofluorocarbon propellant, ethyl alcohol and an inorganic acid which is hydrochloric acid, nitric acid, sulfuric acid or phosphoric acid.

12. An aerosol solution formulation according to claim 11 wherein the HFC propellant is 1,1,1,2-tetrafluoroethane.

13. An aerosol solution formulation according to claim 12 wherein the ethyl alcohol is within the range of about 1.0 to 50.0% wght./wght.

14. An aerosol solution formulation according to claim 11 wherein the inorganic acid is within the range of about 0.00002 to 0.01 Normal.

15. An aerosol solution formulation according to claim 11 wherein the amount of ipratropium bromide is about 0.0187% wght./wght.

16. An aerosol solution formulation according to claim 11 wherein the amount of ipratropium bromide is about 0.0374% wght./wght.

17. An aerosol solution formulation according to claim 11 wherein the amount of ipratropium bromide is about 0.0748% wght./wght.

18. An aerosol solution formulation according to claim 11 wherein the propellant is 1,1,1,2,3,3,3-heptafluoropropane.

19. An aerosol solution formulation comprising 0.001% to 10% wt/wt ipratropium bromide, oxitropium bromide, albuterol, metaproterenol, tiotropium bromide or fenoterol, a hydrofluorocarbon propellant, a cosolvent and an inorganic acid which is hydrochloric acid, nitric acid, sulfuric acid or phosphoric acid.

20. An aerosol solution formulation according to claim 19 wherein the propellant is 1,1,1,2-tetrafluoroethane.

21. An aerosol solution formulation according to claim 20 wherein the cosolvent is ethyl alcohol.

22. An aerosol solution formulation according to claim 19 wherein fenoterol is present in an amount of about 0.192% wght./wght.

23. An aerosol solution formulation according to claim 19 wherein the propellant is 1,1,1,2,3,3,3-heptafluoropropane.

24. An aerosol solution formulation according to claim 19 wherein the cosolvent is ethyl alcohol.

25. A method for stabilizing an aerosol solution formulation wherein the aerosol solution formulation comprises 0.001% to 10% wt/wt ipratropium bromide, 1,1,1,2-tetrafluoroethane and a cosolvent, and wherein the method comprises adding an inorganic acid to the aerosol solution formulation.

26. A method for stabilizing an aerosol solution formulation wherein the aerosol solution formulation comprises 0.001% to 10% wt/wt ipratropium bromide 1,1,1,2-tetrafluoroethane and a cosolvent, and wherein the method comprises adding an inorganic acid to the aerosol solution formulation.

27. The method according to claim 25 wherein the inorganic acid is hydrochloric acid, nitric acid, sulfuric acid, or phosphoric acid.

28. The method according to claim 26 wherein the inorganic acid is hydrochloric acid, nitric acid, sulfuric acid, or phosphoric acid.

* * * * *